United States Patent [19]
Burch et al.

[11] Patent Number: 5,189,046
[45] Date of Patent: Feb. 23, 1993

[54] PROTEIN KINASE C MODULATORS

[75] Inventors: Ronald M. Burch, Silver Spring; Raymond J. Patch, Baltimore; Barry G. Shearer, Baltimore; John J. Perumattam, Baltimore, all of Md.

[73] Assignee: Nova Pharmaceutical Corporation, Baltimore, Md.

[21] Appl. No.: 709,948

[22] Filed: Jun. 4, 1991

Related U.S. Application Data

[63] Continuation-in-part of Ser. No. 657,697, Feb. 19, 1991, abandoned, and a continuation-in-part of Ser. No. 567,219, Aug. 14, 1990, abandoned.

[51] Int. Cl.$^5$ .................. A61K 31/44; A61K 31/445; C07D 211/06; C07D 211/60
[52] U.S. Cl. .................... 514/330; 514/331; 514/354; 514/357; 546/226; 546/229; 546/231; 546/232; 546/245; 546/246; 546/247
[58] Field of Search ............... 546/193, 229, 247, 231, 546/248, 232, 278, 233, 314, 329, 208, 210, 226, 245, 246; 514/330, 340, 341, 332, 354, 357, 331

[56] References Cited
U.S. PATENT DOCUMENTS 4,742,058  5/1988  Yamatsu et al. .................... 546/247
4,762,829  8/1988  Yamatsu et al. .................... 546/246
4,879,300  11/1989  Giordani et al. ................... 514/317
4,923,863  5/1990  Scopes et al. ..................... 514/235.5

OTHER PUBLICATIONS

Rodger et al. "Homocysteine an atherogenic . . . " CA 112:233248h (1990).

Primary Examiner—Alan L. Rotman
Assistant Examiner—Celia Chang
Attorney, Agent, or Firm—Vincent L. Fabiano

[57]  ABSTRACT

PKC modulating compounds of the formula

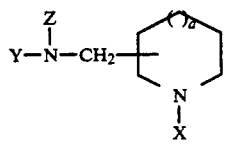

(I)

Also disclosed are pharmaceutical compositions including these compounds which inhibit PKC activity, methods of using these compounds to inhibit PKC activity in mammals, and intermediates useful in preparing the PKC modulating compounds.

11 Claims, No Drawings

PROTEIN KINASE C MODULATORS

BACKGROUND OF THE INVENTION

This application is a continuation-in-part of co-pending application Ser. No. 07/657,697 filed Feb. 19, 1991, now abandoned which is a continuation-in-part of application Ser. No. 07/567,219 filed Aug. 14, 1990, now abandoned.

FIELD OF THE INVENTION

This invention relates to compounds that modulate protein kinase C activity, pharmaceutical compositions including these compounds, and methods for using these compounds to modulate protein kinase C activity in mammals, including humans. The invention also relates to compounds useful as intermediates in preparing the invented protein kinase C modulator compounds.

BACKGROUND INFORMATION

Protein kinase C (calcium/phospholipid protein kinase; PKC) catalyses phosphorylation of the amino acids serene and threonine. PKC is a ubiquitous enzyme in body tissues and is thought to play an important role in neurotransmission, tumor promotion, and cellular proliferation.

Because PKC has wide-ranging physiologic functions, safe and effective modulators of this enzyme will have great therapeutic value. PKC modulators may be useful in treatment of various diseases including inflammatory diseases, proliferative diseases such as psoriasis and various malignancies, neurologic disorders, endocrine disorders, and hypertension.

Compounds that have been identified as PKC inhibitors generally are categorized into five classes. The first class of modulating compounds are lipids which are structurally similar to diacylglycerol. These compounds, however, are not useful as therapeutic agents because they either are excluded from intracellular spaces or are metabolized very rapidly. (May, W., et al., Biochemistry 23:5036, 1984).

The second class of PKC modulating compounds is exemplified by the isoquinoline sulfonamide H-7 and its analogs. (Hidaka, H., et al., Biochemistry 23:5036, 1984). Examples of compounds in this second class include 4-aminomethyl-1-[2,3-(di-n-decyloxy)n-propyl]-4-phenylpiperidine (Shoji, et al. Biochem. Biophys. Res. Commun. 234:590, 1985), several phenothiazine agents (Mori, T., et al. J. Biol. Chem. 255:8378, 1980; Schatzman, R., et al. Biochem. Biophys. Res. Commun. 98:669, 1981), tamoxifen (O'Brien, C., et al. Cancer Res. 45:2462, 1985), quercetin (Srivastava, A., Biochem. Biophys. Res. Commun. 131:1, 1985), amiloride (Besterman, J., et al. J. Biol. Chem. 260:1155, 1985), verapamil (Mori, T., et al. J. Biol. Chem. 255:8378, 1980), adriamycin (Wise, B., et al. J. Biol. Chem. 257:8489, 1982), polymyxin B (Mazzei, G., et al. Biochem. Biophys. Res. Commun. 109:1129, 1982), gangliosides (Kim, J., Neurosci. Res. 15:159, 1986), sangivamycin (Loomis, C. and Bell R., J. Biol. Chem. 263:1682, 1988), retinal (Pataroyo, Immunobiol. 170:305, 1985), and staurosporine (Tamoki, T., et al. Biochem. Biophys. Res. Commun. 135:397, 1986). The compounds in the second class are not specific PKC inhibitors and thus are not useful as therapeutic modulators of PKC activity.

The third class of PKC modulators are peptides thought to bind to the pseudosubstrate site that maintains the enzyme in its inactive form (House, C. and Kemp, B., Science 238:1726, 1987). Peptide inhibitors, however, are excluded from the cytoplasm and therefore are useless as therapeutic agents.

The fourth class of compounds known to modulate PKC are aminoacridines. (Hannum, Y. and Bell, R., J. Biol. Chem. 263:5124, 1988).

The fifth class of compounds that are known to modulate PKC include sphingosine and related sphingolipids. (Bell, R., et al. Cold Spr. Harbor Sym. Quant. Biol. 53:103, 1988). Since sphingosines are major components of biological membranes, and are major dietary components, it is very difficult to use them or their derivatives therapeutically, particularly to treat a systemic disease.

Therefore, despite many years of research there remains a need for safe and effective PKC modulators that are useful therapeutic agents.

SUMMARY OF THE INVENTION

The present invention resides in the discovery that compounds of formula I, below, are selective modulators of PKC. The compounds are useful in treatment of various diseases including inflammatory diseases, proliferative diseases, neurologic disorders, endocrine disorders, and hypertension. Included in the invention are pharmaceutical compositions including the invented compounds and methods of using the invented compounds to modulate PKC.

Presently preferred compounds of the invention include:
3-amino-4-oxo-4-[([1-(1-oxotridecyl)-2-piperidinyl]methyl)amino]butanoic acid phenylmethyl ester,
2-amino-N-([1-(1-oxotridecyl)-2-piperidinyl]methyl)ethanamide,
2,6-diamino-N-([1-(1-oxotridecyl)-2-piperidinyl]methyl)hexanamide,
2-amino-N-([1-(1-oxotridecyl)-2-piperidinyl]methyl)propanamide,
3-amino-N-([1-(1-oxotridecyl)-2-piperidinyl]methyl)propanamide,
4-amino-5-oxo-5-[([1-(1-oxotridecyl)-2-piperidinyl]methyl)amino]pentanamide,
2-amino-N-([1-(1-oxotridecyl)-2-piperidinyl]methyl)-3-(1H-imidazol-4-yl)propanamide,
2-amino-3-hydroxy-N-([1-(1-oxotridecyl)-2-piperidinyl]methyl)propanamide,
2,5-diamino-N-([1-(1-oxotridecyl)-2-piperidinyl]methyl)pentanamide,
2,6-diamino-N-([1-(1-oxododecyl)-2-pyrrolidinyl]methyl)hexanamide,
N-[([1-oxotridecyl)-2-piperidinyl]methyl)amino]-3-methyloxopiperidine,
2,6-diamino-N-([1-(1-oxoundecyl)-2-piperidinyl]methyl)hexanamide,
2,6-diamino-N-([1-(1-oxododecyl)-2-piperidinyl]methyl)hexanamide,
2,6-diamino-N-([1-(1-oxotetradecyl)-2-piperidinyl]methyl)hexanamide,
2,6-diamino-N-([1-(1-oxopentadecyl)-2-piperidinyl]methyl)hexanamide,
2,6-diamino-N-([1-(1-oxohexadecyl)-2-piperidinyl]methyl)hexanamide,
2,6-diamino-N-([1-(1-oxoheptadecyl)-2-piperidinyl]methyl)hexanamide,
2,6-diamino-N-([1-(1-oxooctadecyl)-2-piperidinyl]methyl)hexanamide.
N-([1-(1-oxotetradecyl)-2-piperidinyl]methyl)amine, 2-amino-4-methyl-N-([1-(1-oxotridecyl)-2-piperidinyl]-methyl)pentanamide
2-amino-4-methylthio-N-({1-(1-oxotridecyl)-2piperidinyl}methyl)butanamide
2-amino-N-([1-(1-oxotridecyl)-2-piperidinyl]methyl)-2-phenylpropanamide,
6-amino-N-([1-(1-oxotetradecyl)-2-piperidinyl]methyl)-hexanamide,
2-amino-5-guanidyl-N-([1-(1-oxotridecyl)-2-piperidinyl]methyl)pentanamide,
2,6-diamino-N-([1-(dodecylsulfonyl)-2-piperidinyl]methyl)hexanamide,
2,3-diamino-N-([1-(1-oxotetradecyl)-2-piperidinyl]methyl)propanamide,
2,6-diamino-N-([E-1-oxoocta-9-decenyl)-2-piperidinyl]-methyl)hexanamide,
2,6-diamino-N-([E-1-oxoocta-9-decenyl)-2-piperidinyl]-methyl)hexanamide,
2,6-diamino-N-([Z-1-oxoocta-9-decenyl)-2-piperidinyl]-methyl)hexanamide,
2,6-diamino-N-([1-(1-oxotridecyl)-2-pyrollidinyl]methyl)hexanamide,
(2R)-2,6-diamino-N-{(2R)-[1-(1-oxotridecyl)-2-piperidinyl]methyl}hexanamide
(2R)-2,6-diamino-N-{(2S)-[1-(1-oxotridecyl)-2-piperidinyl]methyl}hexanamide
(2S)-2,6-diamino-N-{(2R)-[1-(1-oxotridecyl)-2-piperidinyl]methyl}hexanamide
(2S)-2,6-diamino-N-{(2S)-[1-(1-oxotridecyl)-2-piperidinyl]methyl}hexanamide The present invention also includes intermediate compounds useful in synthesizing formula (I) compounds.

DETAILED DESCRIPTION OF THE INVENTION

The presently invented compounds that modulate PKC activity have the following formula (I):

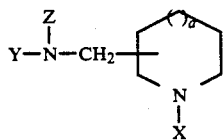

(I)

in which:
a is 0 or 1;
X and Y independently are hydrogen, $C_{10-20}$ alkyl, C(O)E, C(O)$C_{10}$–$C_{20}$ alkyl, C(O)$C_{10}$–$C_{20}$ alkenyl or S($O_2$)$C_{10}$–$C_{20}$ alkyl with the proviso that they are not the same;
E is CH(NH$_2$)FG, CH$_2$FG, or piperidine;
F is $C_{1-10}$ alkyl;
G is NH$_2$, cyclo $C_{3-8}$ alkyl, CO$_2$H, phenyl, guanidino, C(O)NH$_2$, OH, SH, S$C_{1-5}$ alkyl, imidazole or CO$_2$M;
M is $C_{1-8}$ alkyl, phenyl, substituted phenyl, benzyl or substituted benzyl; and
Z is hydrogen or $C_1$–$C_5$ alkyl;
or any pharmaceutically acceptable salt or hydrate thereof.

As used in the specification and claims $C_{I-I'}$ alkyl means a straight or branched, saturated hydrocarbon having I to I' carbon atoms where I and I' are integers, $C_{I-I'}$ alkenyl means a straight or branched unsaturated hydrocarbon having I to I' carbon atoms where I and I' are integers, $C_{I-I'}$ alkoxy means a hydroxy-substituted $C_{I-I'}$ alkyl; also as used herein "modulator" includes agents that stimulate and agents that inhibit PKC activity and substituted phenyl or benzyl means phenyl or benzyl substituted by one or more of $C_{1-4}$ alkyl, halogen, hydroxy, $C_{1-4}$ alkoxy, or amino. Generally, PKC inhibitors are useful as therapeutic agents and PKC stimulators are useful in various basic research and diagnostic assays. The formula used in the specification and claims are intended to include each optical isomer and racemic mixtures.

Preferred formula (I) compounds are compounds in which X is $C_{10-20}$ alkyl, more preferably $C_{12-18}$ alkyl, most preferably $C_{13-17}$ alkyl. Also preferred are compounds in which Y is the carbon terminus of lysine or ornithine.

Formula (I) compounds are prepared from corresponding (aminomethyl)pyridines by processes such as described in the examples and shown in Scheme I, below. The starting (aminomethyl)pyridines and carboxylic acid derivatives are commercially available and can be prepared by known procedures.

Scheme I

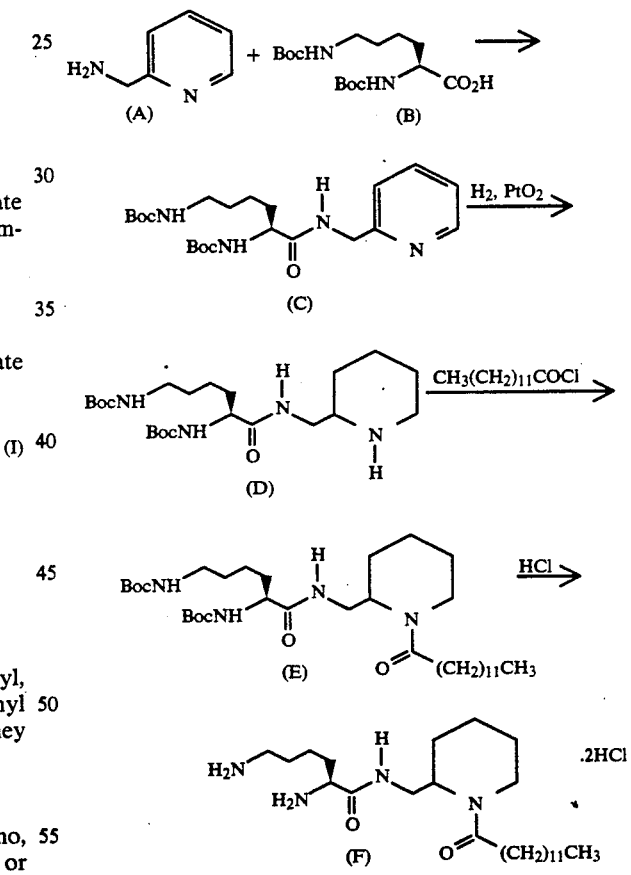

Scheme I illustrates reaction of (aminomethyl)pyridine (A) with a t-butoxycarbonyl (Boc)-protected amino acid (B) to form compounds of formula (C). Formula (C) compounds then are reduced to form compounds (D) which then are reacted with an acid chloride to yield formula (E) compounds. Treatment of compounds (E) with hydrochloric acid yields formula (I) compounds such as compound (F).

Other formula (I) compounds are prepared using known modifications to the Scheme I reaction sequence. Formula (I) compounds wherein Y is other than the deprotected analogue of compound (B) are prepared by replacing formula (B) compounds with appropriate carboxylic acid derivatives. Formula (I) compounds wherein X is other than the $C_{13}$ alkyl shown are prepared by reacting compounds (D) with suitable carboxylic acid or acid chloride derivatives. Compounds wherein X or Y are $S(O_2)E$ are prepared in a similar fashion by replacing the acid chloride in Scheme I with the appropriate sulfonyl chloride.

Pharmaceutically acceptable acid addition salts of the invented compounds are formed with strong or moderately strong organic or inorganic acids by known methods. Exemplary of the acid addition salts which are included in this invention are maleate, fumarate, lactate, oxalate, methanesulfonate, ethansulfonate, benzenesulfonate, tartrate, citrate, hydrochloride, hydrobromide, sulfate, phosphate, quinate, and nitrate salts.

Also included in the invention are pharmaceutical compositions comprising formula I compounds that inhibit PKC activity and suitable carriers in pharmaceutical dosage forms such as capsules, tablets, injectable preparations, ointments, creams, topical reservoirs such as transdermal patches, and suppositories. Solid or liquid carriers can be used. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Ointments and creams are prepared using various well known hydrophilic and hydrophobic bases. Topical reservoirs suitably are prepared using known polymeric materials such as various acrylic-based polymers selected to provide desired release characteristics. Suppositories are prepared from standard bases such as polyethylene glycol and cocoa butter.

The method of this invention of modulating PKC activity comprises administering internally to a subject expected to be benefited thereby an effective amount of a formula I compound. Doses of formula I compounds included in the invented methods and pharmaceutical compositions are an efficacious, nontoxic quantity selected from the range of 0.01 to 100 mg/kg of active compound, preferably 0.1 to 50 mg/kg. Persons skilled in the art using routine clinical testing are able to determine optimum doses. The desired dose is administered to a subject from 1 to 6 or more times daily, orally, rectally, parenterally, or topically.

Activity of Formula I compounds in modulating PKC activity is determined using the phorbol dibutyrate binding and PKC activity assays of Examples 28 and 29, respectively. The assays of these Examples are useful to determine which of the PKC modulating compounds of Formula I inhibit PKC activity. Formula I compounds which stimulate PKC activity are determined using the Example 29 procedure except that phorbol myristateacetate is omitted. The results of these assays demonstrate that Formula I compounds are potent, selective modulators of PKC activity and these assays are well known routine tests useful to distinguish Formula I compounds which inhibit PKC activity from Formula I compounds which stimulate PKC activity.

Assays for measuring PKC activity also are described in: Takai, T. et al., Studies on a Cyclic Nucleotide-independent Protein Kinase and its Proenzyme in Mammalian Tissues, *J. Biol. Chem.* 1977, 252, 7603–7609; Nishizuka, Y., The Role of Protein Kinase C in Cell Surface Signal Transduction and Tumor Production, *Nature* 1984, 308, 693–698; and Kishimoto, A., et al., Activation of Calcium and Phospholipid-dependent Protein Kinase by Diacylglycerol, Its Possible Relationship to Phosphotidylinositol Turnover, *J. Biol. Chem.* 1980, 255, 2273–2276.

The present invention also includes intermediates useful in preparing the invented PKC modulators. The invented intermediates have the following formula (II):

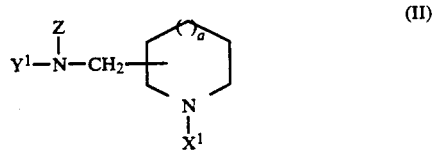

in which:
  a is 0 or 1;
  $X^1$ is hydrogen;
  $Y^1$ is $C_{10-20}$ alkyl, $C(O)E^1$, $C(O)C_{10-20}$ alkyl, $C(O)C_{10-20}$ alkenyl, or $S(O_2)C_{10-20}$ alkyl;
  $E^1$ is $CH(NHR)$, $CH_2FG^1$, or piperidine;
  F is $C_{10-20}$ alkyl;
  $G^1$ is NHR, cyclo $C_{3-8}$ alkyl, $CO_2H$, phenyl, guanidino, $C(O)NHR$, OH, $C_{1-5}$ alkoxy, SH, $SC_{1-5}$ alkyl, imidazole, or $CO_2M$;
  M is $C_{1-8}$ alkyl, phenyl, substituted phenyl, benzyl, or substituted benzyl;
  R is a suitable protecting group; and
  Z is hydrogen or $C_{1-5}$ alkyl.

As used in formula (II) "suitable protecting group" means any easily removed organic functionality which renders the nitrogen atom non-nucleophilic and are well known to those skilled in the art.

Examples of suitable protecting groups are benzyloxycarbonyl, a-fluorenylmethyloxycarbonyl, formyl, and acetyl. A preferred protecting group is t-butoxycarbonyl.

The following examples are illustrative of formula (I) compounds, their preparation and inclusion in pharmaceutical compositions, and tests used to demonstrate their efficacy in modulating PKC activity.

EXAMPLE 1

Preparation of
3-Amino-4-oxo-4-[([1-(1-oxotridecyl)-2-piperidinyl]methyl)amino]butanoic acid phenylmethyl ester hydrochloride To a stirred, cooled (−78° C.) solution of 202 grams (0.92 mol) of di-tert-butyl dicarbonate in 1.5 L of methylene chloride was added 100 grams (0.92 mol) of 2-(aminomethyl)pyridine in 100 mL of methylene chloride dropwise over 0.5 hour. The resulting white suspension was allowed to warm slowly to room temperature while stirring overnight, during which period it became homogeneous. The mixture was washed with water and dried over $MgSO_4$. The solvent was removed at reduced pressure and the crude product was chromatographed on 600 grams of hexane moistened silica gel eluting with 50% ethyl acetate in hexane to provide 188 grams (98%) of 2-[N-(tert-butoxycarbonyl)aminomethyl]pyridine as a light yellow oil.

A solution of 108 g (0.518 mol) of 2-[N-(tert-butoxycarbonyl)aminomethyl]pyridine in 500 mL of ethanol and 50 mL of glacial acetic acid was hydrogenated over 5 grams of $PtO_2$ at 55 psi for 36 hours employing a Parr apparatus. The mixture was cautiously filtered through Celite ® and solvent was removed at reduced pressure. The crude material was dissolved in ethyl acetate, washed with 2N aqueous NaOH, water, brine, and dried over MgSO$_4$. Solvent was removed at reduced pressure and the resulting solid was recrystallized from ethyl acetate/hexane to provide 89.5 grams (80%) of 2-[N-(tert-butoxycarbonyl)aminomethyl]piperidine as a white solid. Mp. 93° C.

To a stirred solution of 13.2 grams (61.5 mmol) of tridecanoic acid in 80 mL of benzene was added 26.2 grams (206 mmol) of oxalyl chloride. After stirring for 20 minutes, the mixture was heated to reflux and maintained at reflux overnight. The mixture was cooled to room temperature and the solvent was removed at reduced pressure to provide 14.3 grams (100%) of tridecanoyl chloride as an orange oil which was used without any further purification.

To a stirred, cooled (0° C.) solution of 14.3 grams (61.4 mmol) of tridecanoyl chloride in 50 mL of methylene chloride was added 7.49 grams (61.3 mmol) of N,N-dimethylaminopyridine. The resulting suspension was stirred for 10 minutes and then 11.0 grams (51.3 mmol) of 2-[N-(tert-butoxycarbonyl)aminomethyl]-piperidine in 50 mL of methylene chloride was added. The mixture was allowed to warm to room temperature while stirring overnight and poured into water. The aqueous layer was extracted with methylene chloride and the combined organic layers were washed with brine and dried over MgSO$_4$. Solvent was removed at reduced pressure and the crude product was chromatographed on 250 grams of silica gel eluting with 25% ethyl acetate in hexane to provide 20.9 grams (99%) of N-(tert-butoxycarbonyl)-N-([1-(1-oxotridecyl)-2-piperidinyl]methyl)amine as a viscous orange oil.

To a stirred solution of 20.9 grams (50.9 mmol) of N-(tert-butoxycarbonyl)-N-([1-(1-oxotridecyl)-2-piperidinyl]methyl)amine in 50 mL of methylene chloride was added 25 mL of trifluoroacetic acid. The mixture was stirred overnight and the solvent was removed at reduced pressure. The resulting residue was dissolved in 1N aqueous NaOH and extracted twice with diethyl ether. The combined organic layers were washed with brine and dried over MgSO$_4$. The solvent was removed at reduced pressure and the crude product was chromatographed on 250 grams of silica gel eluting with 90:10:0.5 chloroform-methanol-ammonium hydroxide to provide 10.1 grams (64%) of N([1-(1-oxotridecyl)-2-piperidinyl]methyl)amine as a viscous yellow oil which slowly solidified upon standing. Mp. 68°–71° C.

To a stirred solution of 2.09 grams (6.73 mmol) of N-([1-(1-oxotridecyl)-2-piperidinyl]methyl)amine in 7.0 mL of methylene chloride was added 681 mg (6.73 mmol) of 4-methylmorpholine. The mixture was stirred for 10 minutes and 3.39 grams (8.06 mmol) of N-tert-butoxycarbonyl-L-aspartic acid-b-benzyl ester-a-N-hydroxysuccinimide ester was added followed by 945 mg (6.99 mmol) of 1-hydroxybenzotriazole hydrate. The orange mixture was stirred overnight and quenched with 177 mg (2.00 mmol) of N,N-dimethylethylenediamine. After stirring for 45 minutes, the mixture was diluted with 125 mL of ethyl acetate and washed sequentially with water, 10% aqueous citric acid, saturated aqueous sodium bicarbonate, water and brine. The organic layer was dried over MgSO$_4$ and solvent was removed at reduced pressure. The resulting crude oil was chromatographed on 125 grams of silica gel eluting with 95:5 chloroform-methanol to provide 2.66 grams (64%) of 3-N-(tert-butoxycarbonyl)amino-4-oxo-4-[([1-(1-oxotridecyl)-2-piperidinyl]methyl)amino]-butanoic acid phenylmethyl ester as a viscous oil.

A solution of 2.59 grams (4.20 mmol) of 3-N-(tert-butoxycarbonyl)amino-4-oxo-4-[([1-(1-oxotridecyl)-2-piperidinyl]methyl)amino]butanoic acid phenylmethyl ester in 10 mL of 4N HCl/dioxane was stirred for 2.5 hours. The solvent was removed at reduced pressure and the resulting residue was dissolved in 1N aqueous NaOH. The aqueous layer was extracted twice with diethyl ether and the combined organic layers were washed with brine and dried over MgSO$_4$. Solvent was removed at reduced pressure and the resulting residue was chromatographed on 65 grams of silica gel eluting with 93:7 chloroform-methanol to provide 1.79 grams (83%) of 3-amino-4-oxo-4-[([1-(1-oxotridecyl)-2-piperidinyl]methyl)amino]butanoic acid phenylmethyl ester as a viscous oil.

To a rapidly stirred solution of 400 mg (0.77 mmol) of 3-amino-4-oxo-4-[([1-(1-oxotridecyl)-2-piperidinyl]methyl)amino]butanoic acid phenylmethyl ester in 6.0 mL of diethyl ether was added 1.5 mL (1.5 mmol) of 1.0N HCl in diethyl ether. The mixture was stirred for 3 minutes and then the resulting solid was collected by vacuum filtration, providing 370 mg (87%) of 3-amino-4-oxo-4-[([1-(1-oxotridecyl)-2-piperidinyl]methyl)amino]butanoic acid phenylmethyl ester hydrochloride as a yellow solid. Mp.>55° C. (decomposition).

This procedure can be used to prepare other aliphatic and aromatic esters such as methyl, ethyl, phenyl and cycohexyl by substituting the appropriate N-tert-butoxy-carbonyl-L-amino acid acid-b- ester-a-N-hydroxysuccinimide ester for N-tert-butoxy- carbonyl-L-aspartic acid-b-benzyl ester-a-N-hydroxysuccinimide ester.

EXAMPLE 2

Preparation of
2-Amino-N-([1-(1-oxotridecyl)-2-piperidinyl]methyl)ethanamide hydrochloride The procedure described in Example 1 was followed substituting N-tert-butoxycarbonyl-glycine-N-hydroxysuccinimide ester for N-tert-butoxycarbonyl-L-aspartic acid-b-benzyl ester-N-a-hydroxysuccinimide ester to provide a 15% overall yield of a yellow solid. Mp.>54° C. (decomposition).

EXAMPLE 3

Preparation of
2,6-Diamino-N-([1-(1-oxotridecyl)-2-piperidinyl]methyl)hexanamide dihydrochloride The procedure described in Example 1 was followed substituting N-a-N-e-di-tert-butoxycarbonyl-L-lysine-N-hydroxysuccinimide ester for N-tert-butoxycarbonyl-L-aspartic acid-b-benzyl ester-N-a-hydroxysuccinimide ester to provide a 15% overall yield of a white solid. Mp.>94° C. (decomposition).

EXAMPLE 4

Preparation of
2-Amino-N-([1-(1-oxotridecyl)-2-piperidinyl]methyl)-propanamide hydrochloride The procedure described in Example 1 was followed substituting N-tert-butoxycarbonyl-L-alanine-N-hydroxysuccinimide ester for N-tert-butoxycarbonyl-L-aspartic acid-b-benzyl ester-N-a-hydroxysuccinimide ester to provide a 17% overall yield of a white solid. Mp. >60° C. (decomposition).

EXAMPLE 5

Preparation of
3-Amino-N-([1-(1-oxotridecyl)-2-piperidinyl]methyl)-propanamide fumarate The procedure for the preparation and coupling of N-([1-(1-oxotridecyl)-2-piperidinyl]methyl)amine with N-tert-butoxycarbonyl-b-alanine-N-hydroxysuccinimide ester and subsequent removal of the N-tert-butoxycarbonyl group was followed as described in Example 1 for N-tert-butoxycarbonyl-L-aspartic acid-b-benzyl ester-N-a-hydroxysuccinimide ester to provide a viscous orange oil in 12% overall yield.

To a stirred solution of 800 mg (2.10 mmol) of the above oil in 5 mL of tetrahydrofuran was added 7.0 mL (2.33 mmol) of 0.33M fumaric acid in tetrahydrofuran. The mixture was stirred for 40 minutes and then concentrated to a volume of approximately 5 mL at reduced pressure. Dilution with diethyl ether provided a white precipitate that was stirred for 30 minutes and then collected by vacuum filtration. Recrystallization from tetrahydrofuran-diethyl ether yielded 320 mg of a white solid. Mp. 60°–74° C.

EXAMPLE 6

Preparation of
4-Amino-5-oxo-5-[([1-(1-oxotridecyl)-2-piperidinyl]methyl)amino]pentanamide hydrochloride The procedure described in Example 1 was followed substituting N-tert-butoxycarbonyl-L-glutamine N-hydroxysuccinimide ester for N-tert-butoxycarbonyl-L-aspartic acid-b-benzyl ester-N-a-hydroxysuccinimide ester to provide a 15% overall yield of a white solid. Mp.>108° C. (decomposition).

EXAMPLE 7

Preparation of
2-Amino-N-([1-(1-oxotridecyl)-2-piperidinyl]methyl)-3-(1H-imidazol-4-yl)propanamide dihydrochloride To a stirred solution of 3.48 grams (11.2 mmol) of a-N-([1-(1-oxotridecyl)-2-piperidinyl]methyl)amine, prepared as described in Example 1, in 20 mL of methylene chloride was added 1.15 grams (11.3 mmol) of 4-methylmorpholine. The mixture was stirred for 5 minutes and 5.00 grams (11.6 mmol) of N-a-N-im-bis-tert-butoxycarbonyl-L-histidine was added followed by 2.22 grams (11.5 mmol) of 1-(3-dimethylaminopropyl)-3-ethylcarbodiimide hydrochloride and 1.65 grams (12.2 mmol) of 1-hydroxbenzotriazole hydrate. The mixture was stirred overnight and then concentrated at reduced pressure. The residue was diluted with ethyl acetate and washed with water, 10% aqueous citric acid, saturated aqueous sodium bicarbonate, water, brine and dried over MgSO4. Solvent was removed at reduced pressure and the crude product was chromatographed on 250 grams of silica gel eluting with 96:4 chloroform-methanol to provide 3.45 grams (48%) of a viscous orange oil.

Removal of the N-tert-butoxycarbonyl groups and hydrochloride salt formation as described in Example 1 afforded 1.82 grams (66%) of a white solid. Mp.>147° C. (decomposition).

EXAMPLE 8

Preparation of
2-Amino-3-hydroxy-N-([1-(1-oxotridecyl)-2-piperidinyl]methyl)propanamide hydrochloride The procedure for the coupling of N-([1-(1-oxotridecyl)-2-piperidinyl]methyl)amine, prepared as described in Example 1, and N-tert-butoxycarbonyl-O-tert-butyl-L-serine was followed as described in Example 7 for N-a-N-im-bis-tert-butoxycarbonyl-L-histidine to provide a yellow oil in 59% yield.

To a stirred solution of 3.40 grams (6.1 mmol) of the above oil in 10 mL of methylene chloride was added 10 mL of trifluoroacetic acid. The mixture was stirred overnight, concentrated at reduced pressure, diluted with ethyl acetate and washed with 1N aqueous NaOH. The aqueous layer was extracted with ethyl acetate and the combined organic layers were then washed with brine and dried over MgSO4. Solvent was removed at reduced pressure and the resulting oil was chromatographed on 85 grams of silica gel eluting with 9:1 chloroform-methanol to afford 1.80 grams (74%) of a viscous yellow oil.

Hydrochloride salt formation as described in Example 1 afforded 1.59 grams (81%) of a white solid. Mp.>61° C. (decomposition).

EXAMPLE 9

Preparation of 2.5-Diamino-N-([1-(1-oxotridecyl)-2-piperidinyl]methyl)pentanamide dihydrochloride The procedure for the preparation and coupling of N-([1-(1-oxotridecyl)-2-piperidinyl]methyl)amine with N-a-N-d-di-benzyloxycarbonyl-L-ornithine-N-hydroxysuccinimide ester was folloed as described in Example 1 for N-tert-butoxycarbonyl-L-aspartic acid-b-benzyl ester-N-a-hydroxysuccinimide ester to provide a viscous oil in 27% overall yield.

To a slurry of 1.00 grams of 10% Pd/C in 10 mL of 1:1 methanol-water under an argon atmosphere was added 2.96 grams (4.27 mmol) of the above oil in 20 mL of methanol. The mixture was hydrogenated at 55 psi overnight using a Parr apparatus and then filtered through a pad of Celite ®. The solvent was removed at reduced pressure and the residue was chromatographed on 20 grams of silica gel eluting with 7:3 chloroform-methanol followed by 1:1 chloroform-methanol to provide 1.55 grams (85%) of as a viscous yellow oil.

Hydrochloride salt formation as described in Example 1 afforded a 87% yield of a white solid. Mp.: 92°–122° C.

EXAMPLE 10

2.6-Diamino-N-([1-(1-oxododecyl)-2-pyrrolidinyl]methyl)hexanamide dihydrochloride To a stirred solution of 25 g (100.4 mmol) of N-benzyloxycarbonyl-L-proline in 500 mL of dry THF was added 200 mL of a 1.0M solution of borane-THF complex at 0° C. The resulting solution was warmed to room temperature and stirred overnight. The excess reagent was quenched by the careful addition of water. The solvent removed and dilute HCl added. The mixture was extracted with ethyl acetate (2×200 mL). The organic extracts were combined, dried over sodium sulfate, filtered and concentrated under reduced pressure to give 22.4 g (95%) of a colorless oil which was used immediately in the next reaction without further purification.

To a stirred solution of 22.4 g (95.3 mmol) of the alcohol in 100 mL of dry pyridine cooled to 0° C. was added 19.0 g (99.7 mmol) of tosyl chloride carefully in small portions. The resulting solution was warmed to room temperature and stirred overnight. It was then poured into ice cold dilute HCl and extracted with ethyl acetate (2×200 mL). The ethyl acetate layers were combined, dried over sodium sulfate, filtered and concentrated under reduced pressure to give 36.0 g (97%) of a light yellow oil which solidified. This was used immediately in the next reaction without further purification.

To a stirred solution of 32.5 g (83.5 mmol) of the above tosylate in 200 mL of dry DMF was added 5.9 g (90.0 mmol) of sodium azide at room temperature. This solution was warmed to 50° C. and stirred overnight. It was then cooled to room temperature, poured into water and extracted with ethyl acetate (2×100 mL). The organic extracts were combined, washed with saturated aqueous sodium bicarbonate, dried over sodium sulfate, filtered and concentrated under reduced pressure to give 20.2 g (93%) of a light yellow oil. This was used immediately in the next reaction without further purification.

To a stirred solution of 20.2 g (77.0 mmol) of the above azide in 200 mL of THF was added 20.9 g (80.0 mmol) of triphenylphosphine at 0° C. The solution was stirred at 0° C. for 1 h, then warmed to room temperature. After the slow addition of 20 mL of saturated methanolic ammonia, the mixture was stirred at room temperature for 72 h. The solution was then concentrated under reduced pressure. Water was added to the residue and it was extracted with ethyl acetate (2×200 mL). The organic extracts were combined, dried over sodium sulfate, filtered and concentrated under reduced pressure to give a dark brown oil. This was purified by flash chromatography (100%) ethyl acetate) to give 14.8 g (81%) of a yellow oil.

To a stirred solution of 14.8 g (63.2 mmol) of the above oil in 200 mL of dry methylene chloride cooled to 0° C. was added 9.8 mL (70.0 mmol) of triethylamine and 5.3 g (70.0 mmol) of di-tert-butyl-di-carbonate and the resulting solution warmed to room temperature and stirred overnight. The solution was then poured into water and the layers allowed to separate. The methylene chloride layer was washed again with water, brine, dried over sodium sulfate, filtered and concentrated under reduced pressure to give 21.0 g (99%) of a yellow oil which was used immediately in the next reaction without further purification.

To a stirred slurry of 2.0 g of 10% palladium on carbon in 20 mL of acetic acid and 2 mL of water was added 21.0 g (62.9 mmol) of the above Cbz-protected Boc-amine in an additional 100 mL of acetic acid and the resulting solution hydrogenated at 60 psi at room temperature overnight. The solution was then filtered through Celite ® and concentrated under reduced pressure. Saturated aqueous sodium bicarbonate was added to the residue and it was extracted with ethyl acetate (2×100 mL). The ethyl acetate layers were combined, dried over sodium sulfate, filtered and concentrated under reduced pressure to give 12.5 g (99%) of a yellow oil. This was used immediately in the next reaction without further purification.

To a stirred solution of 4.0 mL (17.5 mmol) of lauroyl chloride in 75 mL of dry methylene chloride was added 1.5 mL (17.5 mmol) of dry pyridine at 0° C. and the solution stirred for ten minutes. Then 3.0 g (15.0 mmol) of (S)-2-[N-(tert-butoxycarbonyl)aminomethyl]pyrrolidine in 25 mL of methylene chloride was added followed by the addition of 2.1 g (17.5 mmol) of DMAP and the solution stirred at room temperature overnight. The mixture was then poured into water and the aqueous layer extracted with methylene chloride. The organic layers were combined, dried over sodium sulfate, filtered, and concentrated under reduced pressure to give a yellow oil. This was purified by flash chromatography (30% ethyl acetate/hexane) to give 2.9 g (54%) of a light yellow oil.

To 2.9 g (7.9 mmol) of the above oil was added 10 mL of 4N HCl/dioxane and the resulting slurry stirred at room temperature for 1 h. After gas evolution had ceased the dioxane was removed under reduced pressure. Saturated aqueous sodium bicarbonate was added to the residue and it was extracted with ethyl acetate (2×100 mL). The ethyl acetate layers were combined, dried over sodium sulfate, filtered, and concentrated under reduced pressure to give 1.8 g (81%) of a yellow oil. This was used immediately in the next reaction without further purification.

To a stirred solution of 1.8 g (5.7 mmol) of the above aminomethylpyrrolidine in 8 mL of methylene chloride was added 0.63 mL (5.7 mmol) of 4-methylmorpholine and the mixture stirred for 10 min. Then 2.57 g (5.8 mmol) of N-a-N-e-di-tert-butoxycarbonyl-L-lysine-N-hydroxysuccinimide ester was added followed by the addition of 770 mg (5.7 mmol) of 1-hydroxybenzotriazole hydrate and the resulting solution stirred at room temperature overnight. The reaction was quenched by the addition of 0.5 mL of N,N-dimethylethylenediamine and stirred for 1 h. Then 200 mL of ethyl acetate was added and the solution washed successively with water, 10% aqueous citric acid, saturated aqueous sodium bicarbonate, water and brine, dried over sodium sulfate, filtered, and concentrated under reduced pressure. The crude material was purified by flash chromatography (10% methanol, 90% methylene chloride) to give 1.2 g (35%) of a light yellow oil.

To 1.2 g (2.0 mmol) of the above oil was added 10 mL of 4N HCl/dioxane and this mixture was stirred at room temperature for 1 h. After the gas evolution had ceased the dioxane was removed under reduced pressure. The residue was triturated twice with ether and the ether was removed under reduced pressure. The white crystalline residue was dried at 110° C. under vacuum overnight to yield 440 mg (51%) of a hygroscopic white crystalline solid. Analysis calculated for $C_{23}H_{48}Cl_2N_4O_2$: C, 57.13; H, 10.01; N, 11.59; Cl 14.66; Found: C, 47.05; H, 9.99; N, 11.52; Cl, 14.77.

EXAMPLE 11

Preparation of
N-[([1-Oxotridecyl)-2-piperidinyl]methyl)amino]3-methyloxopiperidine hydrochloride The procedure for coupling of N-([1-(1-oxotridecyl)-2-piperidinyl]methyl)amine, prepared as described in Example 1, and N-tert-butoxycarbonyl nipecotic acid was followed as described in Example 7 for N-a-N-im-bis-tert-butoxycarbonyl-L-histidine.§ benzene to provide a viscous orange oil in 41% yield.

Removal of the N-tert-butoxycarbonyl group and hydrochloride salt formation as described in Example 1 afforded a white solid. Analysis calculated for $C_{25}H_{47}N_3O_2 \cdot HCl$: C, 65.54; H, 10.56; N, 9.17; Cl, 7.74. Found C, 65.26; H, 10.59; N, 9.11; Cl 7.70.

EXAMPLE 12

Preparation of
2-Amino-3-phenyl-N-([1-(1-oxotridecyl)-2-piperidinyl]-methyl)propanamide hydrochloride To a stirred, ice-cold solution of 7.5 g (0.069 mol) of 2-aminomethylpyridine and 8.4 g (0.083 mol) of 4-methylmorpholine in 125 mL of methylene chloride was added 25.0 g (0.069 mol) of N-tert-butoxycarbonyl-L-phenylalanine-N-hydroxysuccinimide ester. The mixture was stirred for 3 hours at room temperature and 5 g (0.056 mol) of N,N-dimethylethylenediamine was added. After one hour, the solution was extracted several times with ethyl ether, the extracts combined, dried over potassium carbonate, and concentrated to afford 23.5 g (96%) of a white solid which was recrystallized from ethyl acetate/petroleum ether, mp 109°–110° C.

A solution of 13.5 g (0.038 mol) of this white solid in 150 mL of ethanol and 20 mL of glacial acetic acid was hydrogenated over 4 g of 10% Pd/C at 2000 psi of hydrogen overnight. The mixture was filtered through a pad of Celite ® and the solvent was removed under reduced pressure. The residue was dissolved in water, the solution made basic with 2N sodium hydroxide, and extracted with methylene chloride. The combined organic extracts were dried over potassium carbonate and concentrated under reduced pressure to give 13.1 g (95%) of the product as a white solid which was used without further purification.

A solution of 1.5 g (4.16 mmol) of the above solid, 890 mg (4.16 mmol) of tridecanoic acid, 800 mg (4.16 mmol) of 1-(3-dimethylaminopropyl)-3-ethylcarbodiimide hydrochloride and 20 mg (0.016 mmol) of 4-N,N-dimethylaminopyridine in 10 mL of methylene chloride was stirred overnight at room temperature. The mixture was washed with water, dried over potassium carbonate, and concentrated under reduced pressure. Purification of the resulting residue by flash chromatography (silica gel) eluting with ethyl acetate: hexane (3:1) afforded 1.6 g (69%) of the desired product as a glassy solid.

A solution of 1.6 g (2.87 mmol) of the above solid in 10 mL of 4N hydrochloric acid in dioxane was stirred overnight at room temperature. The reaction was concentrated and the residue partitioned between ether and 2N sodium hydroxide. After further extraction of the aqueous layer with ether, the organic extracts were combined, dried over potassium carbonate, and concentrated under reduced pressure. Purification of the residue by flash chromatography, eluting with ethyl acetate:methanol:ammonium hydroxide (100:5:1) afforded 1.24 g (95%) of the desired product as a viscous oil. This oil was dissolved in 20 mL of ether and an excess of 1.0N hydrochloric acid in ether was added dropwise. The resulting hydrochloride salt was collected by filtration and dried under vacuum. Mp>68° (decomposition).

EXAMPLE 13

An oral dosage form for administering the presently invented compounds is produced by screening, mixing and filling into hard gelatin capsules the ingredients in the proportions shown in Table 1, below:

TABLE I

| Ingredient | Amounts |
| --- | --- |
| 2,6-diamino-N-[(1-(1-oxotridecyl)-2-piperidinyl)methyl]hexanamide | 50 mg |
| magnesium stearate | 5 mg |
| lactose | 75 mg |

EXAMPLE 14

The sucrose, calcium sulfate dihydrate, and formula I compound shown in Table II below, are mixed and granulated in the proportions shown with a 10% gelatin solution. The wet granules are screened, dried, mixed with starch, talc and stearic acid, screened, and compressed into a tablet.

TABLE II

| Ingredients | Amounts |
| --- | --- |
| 2,5-diamino-N-[(1-(oxotridecyl)-2-piperidinyl)methyl]pentanamide | 100 mg |
| calcium sulfate dihydrate | 20 mg |
| sucrose | 150 mg |
| starch | 20 mg |
| talc | 5 mg |
| stearic acid | 3 mg |

EXAMPLE 15

3-Amino-4-oxo-4-{(1-(oxotridecyl)-2-piperidinyl]methyl)amino}butanoic acid phenylmethyl ester hydrochloride (75 mg) is dispersed in 25 ml of normal saline to prepare an injectable preparation.

EXAMPLE 16

Preparation
2-Amino-5-guanidyl-N-([1-(1-oxotridecyl)-2-piperdinyl]methylpentamide dihydrochloride The procedure described in Example 7 was followed substituting N-a-N^G,N^G-tri-tert-butoxycarbonyl-L-arginine for N-aN-im-bis-tert-butoxycarbonyl-L-histidine. benzene to provide a 32% overall yield of a white foam.

Removal of the N-tert-butoxycarbonyl groups and hydrochloride salt formation as described in Example 10 afforded a white solid in 95% yield. Mp.=123° C. (decomposition).

EXAMPLE 17

Preparation of
2,6-Diamino-N-([1-(1-oxoundecyl)-2-piperidinyl]methyl)hexanamide dihydrochloride The procedure described in Example 1 was followed substituting undecanoic acid for tridecanoic acid and N-a-N-e-di-tert-butoxycarbonyl-L-lysine-N-hydroxysuccinimide ester for N-tert-butoxycarbonyl-L-aspartic acid-b-benzyl ester-N-a-hydroxysuccinimide ester to provide a white solid. Mp. 178°–179° C. (decomposition).

EXAMPLE 18

Preparation of
2,6-Diamino-N-([1-(1-oxododecyl)-2-piperidinyl]methyl)hexanamide dihydrochloride The procedure described in Example 1 was followed substituting dodecanoic acid for tridecanoic acid and N-a-N-e-di-tert-butoxycarbonyl-L-lysine-N-hydroxysuccinimide ester for N-tert-butoxycarbonyl-L-aspartic acid-b-benzyl ester-N-a-hydroxysuccinimide ester to provide a white solid. Mp. 196° C. (decomposition).

EXAMPLE 19

Preparation of
2,6-Diamino-N-([1-(1-oxotetradecyl)-2-piperidinyl]methyl)hexanamide dihydrochloride The procedure described in Example 1 was followed substituting tetradecanoic acid for tridecanoic acid and N-a-N-e-di-tert-butoxycarbonyl-L-lysine-N-hydroxysuccinimide ester for N-tert-butoxycarbonyl-L-aspartic acid-b-benzyl ester-N-a-hydroxysuccinimide ester to provide a white solid. Mp. 194° C. (decomposition).

EXAMPLE 20

Preparation of
2,6-Diamino-N-([1-(1-oxopentadecyl)-2-piperidinyl]methyl)-hexanamide dihydrochloride The procedure described in Example 1 was followed substituting pentadecanoic acid for tridecanoic acid and N-a-N-e-di-tert-butoxycarbonyl-L-lysine-N-hydroxysuccinimide ester for N-tert-butoxycarbonyl-L-aspartic acid-b-benzyl ester-N-a-hydroxysuccinimide ester to provide a white solid. Mp. 180°-181° C.

EXAMPLE 21

Preparation of
2,6-Diamino-N-([1-(1-oxohexadecyl)-2-piperidinyl]methyl)hexan-amide dihydrochloride The procedure described in Example 1 was followed substituting hexadecanoic acid for tridecanoic acid and N-a-N-e-di-tert-butoxycarbonyl-L-lysine-N-hydroxysuccinimide ester for N-tert-butoxycarbonyl-L-aspartic acid-b-benzyl ester-N-a-hydroxysuccinimide ester to provide a white solid. Mp. 128° C. (decomposition).

EXAMPLE 22

Preparation of
2,6-Diamino-N-([1-(1-oxoheptadecyl)-2-piperidinyl]methyl)-hexanamide dihydrochloride The procedure described in Example 1 was followed substituting heptadecanoic acid for tridecanoic acid and N-a-N-e-di-tert-butoxycarbonyl-L-lysine-N-hydroxysuccinimide ester for N-tert-butoxycarbonyl-L-aspartic acid-b-benzyl ester-N-a-hydroxysuccinimide ester to provide a white solid. Mp. 131° C. (decomposition).

EXAMPLE 23

Preparation of
2,6-Diamino-N-([1-(1-oxooctadecyl)-2-piperidinyl]methyl)hexan-amide dihydrochloride The procedure described in Example 1 was followed substituting octadecanoic acid for tridecanoic acid and N-a-N-e-di-tert-butoxycarbonyl-L-lysine-N-hydroxysuccinimide ester for N-tert-butoxycarbonyl-L-aspartic acid-b-benzyl ester-N-a-hydroxysuccinimide ester to provide a white solid. Mp. 128°-133° C.

EXAMPLE 24

Preparation of
(2S)-2,6-Diamino-N-{(2S)-[1-(1-oxotridecyl)-2-piperidinyl]methyl}hexanamide To a suspension of 9.0 g (70.2 mmol) of (S)-piperidine-2-carboxamide (prepared by the method of Geotz Hardtmann, William Houlihan and Rudolf Giger, U.S. Pat. No. 4,760,065) in 100 mL of methylene chloride was added 24.0 g (140.4 mmol) of benzyl bromide and 7.2 g (70.2 mmol) of triethylamine. The mixture was stirred at room temperature for 24 h and washed with 1N aqueous sodium hydroxide. The organic layer was dried over anhydrous sodium sulfate and solvent was removed at reduced pressure. The residue was purified by silica gel chromatography using hexane:ethyl acetate (1:1) as eluent to give (S)-N-benzyl-piperidine-2-carboxamide (12.2 g, 80%), mp 103°-104° C., specific rotation= −90.7° (c=2.5, ethanol).

To a solution of 230 mL (0.23 mmol) of 1M lithium aluminum hydride in THF was added over 20 min a solution of (S)-N-benzylpiperidine-2-carboxamide in 150 mL of THF. The mixture was refluxed for 5 h, diluted with 500 ml of THF, cooled to −78° C. and quenched with a solution of 48 mL 1N aqueous sodium hydroxide in 200 mL THF. The resulting slurry was filtered through a Celite ® pad and concentrated at reduced pressure to yield (S)-N-benzyl-2-aminomethylpiperidine (10.9 g, 89%).

To a solution of 9.0 g (26 mmol) of Boc-(S)-Lys(Boc)-OH and 5.3 g (26 mmol) of (S)-N-benzyl-2-aminomethylpiperidine in 80 mL of dry methylene chloride was added sequentially 3.5 g (26 mmol) 1-hydroxybenzotriazole hydrate, 2.6 g (26 mmol) N-methylmorpholine, and 5.0 g (26 mmol) 1-(3-dimethylaminopropyl)-3-ethylcarbodiimide hydrochloride. The reaction mixture was stirred at room temperature for 5 h, diluted with methylene chloride and washed with 10% NaHCO$_3$ solution. The organic layer was dried over sodium sulfate, concentrated at reduced pressure and chromatographed on silica gel using hexane:ethyl acetate:methanol (1:1:0.1) as eluent. The coupled product was obtained in 87% yield (12 g) as a white foam-like solid, specific rotation= −49° (c=2.1, ethanol).

To a solution of 12.0 g (22.5 mmol) of the coupled product in 100 mL of methanol was added 5 g of 10% Pd/C and the mixture was hydrogenated in a Parr shaker at room temperature at 65 psi for 7 h. The mixture was filtered through a Celite ® pad and the solvent removed at reduced pressure to give 10 g (100%) of debenzylated product.

To a solution of 7.5 g (17 mmol) of the above compound and 13.6 g (17 mmol) of tridecanoic acid in 100 ml of dry methylene chloride was added sequentially 2.3 g (17 mmol) 1-hydroxybenzotriazole hydrate, 1.7 g (17 mmol) N-methylmorpholine, and 3.3 g (17 mmol) 1-(3-dimethylaminopropyl)-3-ethylcarbodiimide hydrochloride. The mixture was stirred at room temperature overnight, diluted with methylene chloride and washed with 10% aqueous sodium bicarbonate solution. The organic layer was dried over sodium sulfate, concentrated at reduced pressure and the residue chromatographed on silica gel using hexane:ethyl acetate (1:1) as eluent. The product was obtained in 87% yield (10.7 g) as an oil, specific rotation= −23.6° (c=3, ethanol).

The above compound (1.95 g, 3 mmol) was dissolved in 15 mL of dioxane and treated with 5 ml (20 mmol) of 4M HCl solution in dioxane. After 20 h at room temperature the suspension was diluted with 200 ml ether. The finely powdered solids were collected by filtration and dried to yield 1.3 g (90%) of (2S)-2,6-diamino-N-(2S)-([1-(1-oxotridecyl)-2-piperidinyl]methyl)hexanamide, specific rotation= −11.0° (c=2, chloroform). Anal calcd for $C_{25}H_{50}N_4O_2 \cdot 2HCl \cdot 0.75\ H_2O$: C, 57.19; H, 10.20; N.10.66; Cl, 13.50. Found: C, 57.20; H, 10.22; N.10.72; Cl, 13.58.

EXAMPLE 25

Preparation of
(2R)-2,6-Diamino-N-{(2S)-[1-(1-oxotridecyl)-2-piperidinyl]methyl}hexanamide This compound was prepared by the method of example 24 using Boc-(R)-Lys(Boc)-OH instead of Boc-(S)-Lys(Boc)-OH to give the title compound, specific rotation = −8.8° (c=2, chloroform).

EXAMPLE 26

Preparation of
(2R)-2,6-Diamino-N-{(2R)-[1-(1-oxotridecyl)-2-piperidinyl]methyl}hexanamide This compound was prepared by the method of example 24 using (R)-piperidine-2-carboxamide (prepared by the method of Geotz Hardtmann, William Houlihan and Rudolf Giger, U.S. Pat. No. 4,760,065) instead of (R)-piperidine-2-carboxamide give the title compound, specific rotation = +10.9° (c=1.0, chloroform)

EXAMPLE 27

Preparation of
(2S)-2,6-Diamino-N-{(2R)-[1-(1-oxotridecyl)-2-piperidinyl]methyl}hexanamide This compound was prepared by the method of example 24 using (R)-piperidine-2-carboxamide (prepared by the method of Geotz Hardtmann, William Houlihan and Rudolf Giger, U.S. Pat. No. 4,760,065) instead of (R)-piperidine-2-carboxamide to give the title compound, specific rotation = +8.9. (c=1.4, chloroform).

EXAMPLE 28

$^3$H-Phorbol Dibutyrate Binding

The ability of active compounds to inhibit the binding of phorbol ester to protein kinase C from mouse brains was measured as follows. Mouse brains were homogenized in ice-cold 50 mM Tris buffer, pH 7.4, containing 0.5 mM $CaCl_2$, in a 15 mL Dounce homogenizer with 10 gentle strokes. The homogenate was centrifuged at 100,000×g for 1 hour at 4° C. The pellets were resuspended in 25 mL of the same ice-cold buffer and protein concentration was adjusted to 0.4 mg/mL. To each binding tube was added 200 mL of the buffer, 100 mL of [20-$^3$H]Phorbol 12,13-dibutyrate, 8 mM final concentration in assay, 50 mL of test drug or displacing ligand, 50 uL of 50 mM Tris, pH 7.4 at 25° C. containing 1% bovine serum albumin, and 100 mL enzyme preparation. Tubes were incubated at 37° C. for 30 minutes, then terminated by filtration onto Whatman GF/B glass fiber filters followed by washing with 2 mL ice-cold 50 mM Tris, pH 7.4, four times. Nonspecific binding was defined as that binding occurring in the presence of 1 mM phorbol ester. Percent inhibition was determined for each inhibitor candidate, and $IC_{50}$ values were determined using the computer program "EBDA". Results are reported in Table III.

| Inhibition of $^3$H-phorbol dibutyrate binding | | |
|---|---|---|
| Compound | % inhibition @ 100 μM | $IC_{50}$, μM |
| 3-amino-4-oxo-4-[((1-(1-oxotridecyl)-2-piperidinyl]-methyl)amino]butanoic acid phenylmethyl ester hydrochloride | 2 | — |
| 2-amino-N-([1-(1-oxotridecyl)-2-piperidinyl]methyl)ethanamide hydrochloride | 21 | — |
| 2,6-diamino-N-([1-(1-oxotridecyl)-2-piperidinyl]methyl)hexanamide dihydrochloride | 22 | 191 |
| 2-amino-N-([1-(1-oxotridecyl)-2-piperidinyl]methyl)propanamide hydrochloride | 49 | — |
| 3-amino-N-([1-(1-oxotridecyl)-2-piperidinyl]methyl)propanamide fumarate | 45 | 139 |
| 4-amino-5-oxo-5-[((1-(1-oxotridecyl)-2-piperidinyl]methyl)amino]pentanamide hydrochloride | 17 | — |
| 2,6-diamino-N-([1-(1-oxotridecyl)-2-piperidinyl]methylhexanamide dihydrochloride | 47 | 133 |
| 2-amino-N-([1-(1-oxotridecy)-2-piperidinyl]methyl)-3-(1H-imidazol-4-yl)propanamide dihydrochloride | 28 | 343 |
| 2-amino-3-hydroxy-N-([1-1(oxotridecyl)-2-piperidinyl]methyl)propanamide hydrochloride | 9 | — |
| N[([1-oxotridecyl)-2-piperidinyl]methyl)amino] 3-methyloxopiperidine hydrochloride | 34 | 157 |

EXAMPLE 29

The ability of active compounds to inhibit PKC was determined with an assay that measures the inhibition of the phosphorylation of histone by the enzyme in tissue homogenates. Protein kinase C from mouse brain was used in the screening protocol since it contains several isozymes of the enzyme. The tissue was prepared by homogenizing two mouse brains minus the cerebelli in 5 ml of 25 mM Tris-HCl,pH 7.4, containing 2 mM ethylenediamine tetraacetic acid (EDTA) and 1 mM ethylene glycol tetraacetic acid (EGTA), using a polytron at setting 5 for 15 seconds. The homogenate was centrifuged for 1 hour at 50,000×g at 4° C. The supernatant was used as the source of enzyme. The standard reaction mixture (250 μl) contained 20 mM Tris-HCl,pH 7.5, 10 mM Mg $(CH_3COO)_2$, 400 μM $CaCl_2$, 0.1 mM EGTA, 10 mM [γ-$^{32}$P] ATP (1200 cpm/pmol), 100 μg/ml phosphatidylserine, 10 μM histone, 1 μM phorbol 12-myristate-13-acetate, 10 μl enzyme preparation and 25 μl water or test drug. The mixture was incubated at 30° C. for 5 minutes. Mixtures were removed to an ice-bath, a 50 μl aliquot of each was added to Whatman P81 paper and washed in 10% TCA for 20 minutes. The paper was then washed with ethanol, followed by ethyl ether and finally air dryed. PKC activity was quantitated by liquid scintillation counting. Approximately 80% of the phosphorylation in this assay is dependent on PKC.

Protein kinase A activity was determined as follows. Protein kinase A catalytic subunit was purchased from Sigma Chemical Company. To microfuge tubes were added 150 μl of assay buffer, 10 μl of 20 mg/μl histone Type III-S, 25 μl of assay buffer or test drug, 10 μl enzyme (4 ng of catalytic subunit or 8 ng intact enzyme plus or minus 100 mM dibutyryl-cAMP), and 25 μl of 6.78 mg/10 mL (800 mCi/μl) $^{32}$P-ATP. Incubation was at 30° C. for 5 minutes, then the assay was completed as described for protein kinase C above. The results are reported in Table IV. As indicated in Table IV, the active compounds described herein significantly inhibit phosphorylation by PKC, with $IC_{50}$ values ranging from 13 micromolar for 2,6-diamino-N-([1-(1-oxotridecyl)-2-piperdinyl]methyl)hexanamide to 92 micromolar for 3-amino-4-oxo-4-[([1-(1-oxotridecyl)-2-piperidinyl]methyl)aminobutanoic acid phenylmethyl ester. In contrast, none of the compounds inhibited the phosphorylation of histone by protein kinase A which is reported as percent inhibition at the maximum concentration tested 100 μM. These data demonstrate that the active compounds are selective inhibitors of PKC and not general phosphorylation inhibitors.

TABLE IV

Inhibition of protein kinase phosphorylation of histone

| Compound | PKC IC$_{50}$, μM | PKA |
|---|---|---|
| Staurosporine (reference standard) | 0.0027 | 0.0027 (IC$_{50}$, μM) |
| H-7 (reference standard) | 9 | 28 (IC$_{50}$, μM) |
| Sphingosine (reference standard) | 15 | 88% |
| 3-amino-4-oxo-4-[([1-(1-oxotridecyl)-2-piperidinyl]methyl)aminobutanoic acid phenylmethyl ester hydrochloride | 92 | 0 |
| 2-amino-N-([1-(1-oxotridecyl)-2-piperidinyl]methyl)ethanamide hydrochloride | 51 | 0 |
| 2,6-diamino-N-([1-(1-oxotridecyl)-2-piperidinyl]methyl)hexanamide dihydrochloride | 13 | 0 |
| 2-amino-N-([1-(1-oxotridecyl)-2-piperidinyl]methyl)propanamide hydrochloride | 52 | 0 |
| 3-amino-N-([1-oxotridecyl)-2-piperidinyl]methyl)propanamide fumarate | 36 | 0 |
| 4-amino-5-oxo-5-[([1-(1-oxotridecyl)-2-piperidinyl]methyl)propanamide hydrochloride | 72 | 0 |
| 2-amino-N-([1-(1-oxotridecyl)-2-piperidinyl]methyl)-3-(1H-imidazol-4-yl)propanamide dihydrochloride | 60 | 0 |
| 2-amino-3-hydroxy-N-([1-(1-oxotridecyl)-2-piperidinyl]methyl)-propanamide hydrochloride | 44 | 0 |
| 2,5-diamino-N-([1-(1-oxotridecyl)-2-piperidinyl]methyl)pentanamide dihydrochloride | 18 | 0 |
| 2,6-diamino-N-([1-(1-oxododecyl)-2-pyrrolidinyl]methyl)hexanamide dihydrochloride | 46 | 0 |
| N-[([1-(1-oxotridecyl)-2-piperidinyl]methyl)amino] 3-methyloxopiperidine hydrochloride | 29 | 0 |

As indicated in Table IV, the invented compounds are potent, selective PKC inhibitors. The data indicate that the compounds are useful to treat various inflammatory diseases, proliferative diseases, various malignancies, neurologic disorders, endocrine disorders, and hypertension.

While the preferred embodiments of the invention are illustrated by the above it is to be understood that the invention is not limited to the precise instructions contained herein and that the right to all modifications coming within the scope of the following claims is reserved.

Presently contemplated equivalents of formula (I) compounds include PKC modulating compounds similar to formula (I) compounds substituted on the non-ring nitrogen by the carbon terminal of amino acids not included in the formula (I) definition.

What is claimed is:

1. A protein kinase C modulator compound represented by the formula:

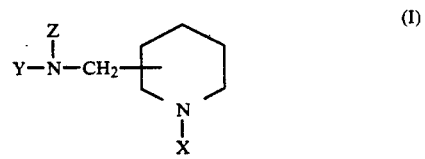

in which:

X and Y independently are, C$_{10-20}$ alkyl, C(O)E, C(O)C$_{10}$–C$_{20}$ alkyl, C(O)C$_{10}$–C$_{20}$ alkenyl or S(O$_2$)C$_{10}$–C$_{20}$ alkyl with the proviso that they are not the same;

E is CH(NH$_2$)FG or CH$_2$FG;

F is C$_{1-10}$ alkylene;

G is NH$_2$, cyclo C$_{3-8}$ alkyl, CO$_2$H, phenyl, guanidino, C(O)NH$_2$, OH, SH, SC$_{1-5}$ alkyl, or CO$_2$M;

M is C1-8 alkyl, phenyl, phenyl substituted by one or more C$_{1-4}$ alkyl, halogen, hydroxy, C$_{1-4}$ alkoxy, or amino, benzyl or benzyl substituted by one or more C$_{1-4}$ alkyl, halogen, hydroxy, C$_{1-4}$ alkoxy, or amino; and Z is hydrogen or C$_1$–C$_5$ alkyl;

or any pharmaceutically acceptable salt or hydrate thereof.

2. A compound of claim 1 wherein Y is C(O)E and E is CH(NH$_2$)FG.

3. A compound of claim 3 wherein X is C$_{10-20}$ alkyl.

4. A compound of claim 3 that is 2,6-diamino-N-[(1-(1-oxotridecy)-2-piperidinyl)methyl]hexanamide, 2,5-diamino-N-[(1-(oxotridecyl)-2-piperidinyl)methyl]pentanamide, or pharmaceutically acceptable salts or hydrates thereof.

5. A compound of claim 1 that is:

3-amino-4-oxo-4-[([1-(1-oxotridecyl)-2-piperidinyl]methyl)amino]butanoic acid phenylmethyl ester, 2-amino-N-([1-(1-oxotridecyl)-2-piperidinyl]methyl)ethanamide, 2-amino-N-([1-(1-oxotridecyl)-2-piperidinyl]methyl)propanamide, 3-amino-N-([1-(1-oxotridecyl)-2-piperidinyl]methyl)propanamide, 4-amino-5-oxo-5-[([1-(1-oxotridecyl)-2-piperidinyl]methyl)amino]pentanamide, 2-amino-3-hydroxy-N-([1-(1-oxotridecyl)-2-piperidinyl]methyl)propanamide, N-[([1-oxotridecyl)-2-piperidinyl]methyl)amino]3-methyloxopiperidine, 2-amino-3-phenyl-N-([1-(1-oxotridecyl)-2-piperidinyl]methyl)propanamide, 2-amino-5-guanidyl-N-([1-(oxotridecyl]-2-piperidinyl]methyl)pentamide, 2,6-diamino-N-([1-(1-oxoundecyl)-2-piperidinyl]methyl)hexanamide, 2,6-diamino-N-([1-(1-oxododecyl)-2-piperidinyl]methyl)hexanamide, 2,6-diamino-N-([1-(1-oxotetradecyl)-2-piperidinyl]methyl)hexanamide, 2,6-diamino-N-([1-(1-oxopentadecyl)-2-piperidinyl]methyl)hexanamide, 2,6-diamino-N-([1-(1-oxohexadecyl)-2-piperidinyl]methyl)hexanamide, 2,6-diamino-N-([1-(1-oxoheptadecyl)-2-piperidinyl]methyl)hexanamide, 2,6-diamino-N-([1-(1-oxooctadecyl)-2-piperidinyl]methyl)hexanamide, N-([1-(1-oxotetradecyl)-2-piperidinyl]methyl)amine, 2-amino-4-methyl-N-([1-(1-oxotridecyl)-2-piperidinyl]methyl)pentanamide
2-amino-4-methylthio-N-([1-(1-oxotridecyl)-2-piperidinyl]methyl)butanamide,
2-amino-N-([1-(1-oxotridecyl)-2-piperidinyl]methyl)-2-phenylpropanamide,
6-amino-N-([1-(1-oxotetradecyl)-2-piperidinyl]methyl)hexanamide,
2-amino-5-guanidyl-N-([1-(1-oxotridecyl)-2-piperidinyl]methyl)pentanamide,
2,6-diamino-N-([1-(dodecylsulfonyl)-2-piperidinyl]methyl)hexanamide,
2,3-diamino-N-([1-(1-oxotetradecyl)-2-piperidinyl]methyl)propanamide,
2,6-diamino-N-([E-1-oxoocta-9-decenyl)-2-piperidinyl]methyl)hexanamide,
2,6-diamino-N-([Z-1-oxoocta-9-decenyl)-2-piperidinyl]methyl)hexanamide,
(2R)-2,6-diamino-N-{(2R)-[1-(1-oxotridecyl)-2-piperidinyl]methyl}hexanamide,
(2R)-2,6-diamino-N-{(2S)-[1-(1-oxotridecyl)-2-piperidinyl]methyl}hexanamide,
(2S)-2,6-diamino-N-{(2R)-[1-(1-oxotridecyl)-2-piperidinyl]methyl}hexanamide,
(2S)-2,6-diamino-N-{(2S)-[1-(1-oxotridecyl)-2-piperidinyl]methyl}hexanamide, or
pharmaceutically acceptable salts or hydrates thereof.

6. A pharmaceutical composition useful for inhibiting PKC activity in mammals comprising a pharmaceutical carrier and a PKC inhibiting compound of claim 1.

7. A pharmaceutical composition of claim 6 wherein the compound is 2,6-diamino-N-[(1-(1-oxotridecyl)-2-piperidinyl)methyl]hexanamide, 2,5-diamino-N-[(1-(oxotridecyl)-2-piperidinyl)methyl]pentanamide, or pharmaceutically acceptable salts or hydrates thereof.

8. A pharmaceutical composition of claim 6 wherein the compound is
3-amino-4-oxo-4-[([1-(1-oxotridecyl)-2-piperidinyl]methyl)amino]butanoic acid phenylmethyl ester,
2-amino-N-([1-(1-oxotridecyl)-2-piperidinyl]methyl)ethanamide,
2-amino-N-([1-(1-oxotridecyl)-2-piperidinyl]methyl)propanamide,
3-amino-N-([1-(1-oxotridecyl)-2-piperidinyl]methyl)propanamide,
4-amino-5-oxo-5-[([1-(1-oxotridecyl)-2-piperidinyl]methyl)amino]pentanamide,
2-amino-3-hydroxy-N-([1-(1-oxotridecyl)-2-piperidinyl]methyl)propanamide,
N-[([1-oxotridecyl)-2-piperidinyl]methyl)amino]3-methyloxopiperidine,
2-amino-3-phenyl-N-([1-(1-oxotridecyl)-2-piperidinyl]methyl)propanamide,
2-amino-5-guanidyl-N-([1-(oxotridecyl)-2-piperidinyl]methyl)pentamide,
2,6-diamino-N-([1-(1-oxoundecyl)-2-piperidinyl]methyl)hexanamide,
2,6-diamino-N-([1-(1-oxododecyl)-2-piperidinyl]methyl)hexanamide,
2,6-diamino-N-([1-(1-oxotetradecyl)-2-piperidinyl]methyl)hexanamide,
2,6-diamino-N-([1-(1-oxopentadecyl)-2piperidinyl]methyl)hexanamide,
2,6-diamino-N-([1-(1-oxohexadecyl)-2-piperidinyl]methyl)hexanamide,
2,6-diamino-N-([1-(1-oxoheptadecyl)-2-piperidinyl]methyl)hexanamide,
2,6-diamino-N-([1-(1-oxooctadecyl)-2-piperidinyl]methyl)hexanamide,
N-([1-(1-oxotetradecyl)-2-piperidinyl]methyl)amine,
2-amino-4-methyl-N-([1-(1-oxotridecyl)-2-piperidinyl]methyl)pentanamide
2-amino-4-methylthio-N-([1-(1-oxotridecyl)-2-piperidinyl]methyl)butanamide,
2-amino-N-([1-(1-oxotridecyl)-2-piperidinyl]methyl)-2-phenylpropanamide,
6-amino-N-([1-(1-oxotetradecyl)-2-piperidinyl]methyl)hexanamide,
2-amino-5-guanidyl-N-([1-(1-oxotridecyl)-2-piperidinyl]methyl)pentanamide,
2,6-diamino-N-([1-(dodecylsulfonyl)-2-piperidinyl]methyl)hexanamide,
2,3-diamino-N-([1-(1-oxotetradecyl)-2-piperidinyl]methyl)propanamide,
2,6-diamino-N-([E-1-oxoocta-9-decenyl)-2-piperidinyl]methyl)hexanamide,
2,6-diamino-N-([Z-1-oxoocta-9-decenyl)-2-piperidinyl]methyl)hexanamide,
(2R)-2,6-diamino-N-{(2R)-[1-(1-oxotridecyl)-2-piperidinyl]methyl}hexanamide,
(2R)-2,6-diamino-N-{(2S)-[1-(1-oxotridecyl)-2-piperidinyl]methyl}hexanamide,
(2S)-2,6-diamino-N-{(2R)-[1-(1-oxotridecyl)-2-piperidinyl]methyl}hexanamide,
(2S)-2,6-diamino-N-{(2S)-[1-(1-oxotridecyl)-2-piperidinyl]methyl}hexanamide, or
pharmaceutically acceptable salts or hydrates thereof.

9. A method for inhibiting PCK activity in mammals that comprises administering to a subject an amount of a PKC inhibiting compound of claim 1 effective to produce anti-inflammatory, anti-convulsant, or cerebral protective activity.

10. A method of claim 9 wherein the compound is 2,6-diamino-N-[(1-(1-oxotridecyl)-2-piperidinyl)methyl]hexanamide, 2,5-diamino-N-[(1-(oxotridecyl)-2-piperidinyl)methyl]pentanamide, or pharmaceutically acceptable salts or hydrates thereof.

11. A method of claim 9 wherein the compound is
3-amino-4-oxo-4-[([1-(1-oxotridecyl)-2-piperidinyl]methyl)amino]butanoic acid phenylmethyl ester,
2-amino-N-([1-(1-oxotridecyl)-2-piperidinyl]methyl)ethanamide,
2-amino-N-([1-(1-oxotridecyl)-2-piperidinyl]methyl)propanamide,
3-amino-N-([1-(1-oxotridecyl)-2-piperidinyl]methyl)propanamide,
4-amino-5-oxo-5-[([1-(1-oxotridecyl)-2-piperidinyl]methyl)amino]pentanamide,
2-amino-3-hydroxy-N-([1-(1-oxotridecyl)-2-piperidinyl]methyl)propanamide,
N-[([1-oxotridecyl)-2-piperidinyl]methyl)amino]3-methyloxopiperidine,
2-amino-3-phenyl-N-([1-(1-oxotridecyl)-2-piperidinyl]methyl)propanamide,
2-amino-5-guanidyl-N-([1-(oxotridecyl]-2-piperidinyl]methyl)pentamide,
2,6-diamino-N-([1-(1-oxoundecyl)-2-piperidinyl]methyl)hexanamide,
2,6-diamino-N-([1-(1-oxododecyl)-2-piperidinyl]methyl)hexanamide,
2,6-diamino-N-([1-(1-oxotetradecyl)-2-piperidinyl]methyl)hexanamide,
2,6-diamino-N-([1-(1-oxopentadecyl)-2-piperidinyl]methyl)hexanamide, 2,6-diamino-N-([1-(1-oxohexadecyl)-2-piperidinyl]methyl)hexanamide,
2,6-diamino-N-([1-(1-oxoheptadecyl)-2-piperidinyl]methyl)hexanamide,
2,6-diamino-N-([1-(1-oxooctadecyl)-2-piperidinyl]methyl)hexanamide,
N-([1-(1-oxotetradecyl)-2-piperidinyl]methyl)amine,
2-amino-4-methyl-N-([1-(1-oxotridecyl)-2-piperidinyl]methyl)pentanamide
2-amino-4-methylthio-N-([1-(1-oxotridecyl)-2-piperidinyl]methyl)butanamide,
2-amino-N-([1-(1-oxotridecyl)-2-piperidinyl]methyl)-2-phenylpropanamide,
6-amino-N-([1-(1-oxotetradecyl)-2-piperidinyl]methyl)hexanamide,
2-amino-5-guanidyl-N-([1-(1-oxotridecyl)-2-piperidinyl]methyl)pentanamide,
2,6-diamino-N-([1-(dodecylsulfonyl)-2-piperidinyl]methyl)hexanamide,
2,3-diamino-N-([1-(1-oxotetradecyl)-2-piperidinyl]methyl)propanamide,
2,6-diamino-N-([E-1-oxoocta-9-decenyl)-2-piperidinyl]methyl)hexanamide,
2,6-diamino-N-([Z-1-oxoocta-9-decenyl)-2-piperidinyl]methyl)hexanamide,
(2R)-2,6-diamino-N-{(2R)-[1-(1-oxotridecyl)-2-piperidinyl]methyl}hexanamide,
(2R)-2,6-diamino-N-{(2S)-[1-(1-oxotridecyl)-2-piperidinyl]methyl}hexanamide,
(2S)-2,6-diamino-N-{(2R)-[1-(1-oxotridecyl)-2-piperidinyl]methyl}hexanamide,
(2S)-2,6-diamino-N-{(2S)-[1-(1-oxotridecyl)-2-piperidinyl]methyl}hexanamide, or
pharmaceutically acceptable salts or hydrates thereof.

* * * * *